United States Patent
Travers et al.

(10) Patent No.: US 6,921,668 B2
(45) Date of Patent: Jul. 26, 2005

(54) DETERMINING INFECTIONS IN LIQUID SAMPLES BY DETECTING SHORT-CHAIN FATTY ACIDS AND AMMONIA IN THE HEADSPACE ASSOCIATED WITH THE LIQUID SAMPLE USING POLYMER SENSORS

(75) Inventors: Paul James Travers, Manchester (GB); Martin James Henery, Alderley Edge (GB); John Charles Plant, Stone (GB); Sean Sydney Aiken, Stoke on Trent (GB); Andrew John Tummon, Middlewich (GB); Alexander Samuel McNeish, Nr Nantwich (GB); Janet Elizabeth Manning, Goostrey (GB); Amjad Nissar Chaudry, Manchester (GB)

(73) Assignee: Osmetech PLC (GB)

( * ) Notice: Subject to any disclaimer, the term of this patent is extended or adjusted under 35 U.S.C. 154(b) by 173 days.

(21) Appl. No.: 10/221,920

(22) PCT Filed: Nov. 26, 2001

(86) PCT No.: PCT/GB01/05197

§ 371 (c)(1),
(2), (4) Date: Sep. 16, 2002

(87) PCT Pub. No.: WO02/42488

PCT Pub. Date: May 30, 2002

(65) Prior Publication Data

US 2004/0106210 A1 Jun. 3, 2004

Related U.S. Application Data

(60) Provisional application No. 60/335,308, filed on Nov. 15, 2001.

(30) Foreign Application Priority Data

Nov. 24, 2000 (GB) .............................................. 0028668

(51) Int. Cl.⁷ .............................................. G01N 33/00
(52) U.S. Cl. ........................ 436/129; 113/128; 113/149; 113/161
(58) Field of Search ................................ 436/113, 128, 436/129, 149, 161

(56) References Cited

U.S. PATENT DOCUMENTS

5,788,687 A * 8/1998 Batich et al. ............ 604/890.1
6,244,096 B1 * 6/2001 Lewis et al. ................ 73/23.2

FOREIGN PATENT DOCUMENTS

| WO | 95 33848 | 12/1995 |
| WO | 99 66304 A1 | 12/1999 |
| WO | 00 53798 A1 | 9/2000 |

OTHER PUBLICATIONS

Bogaard et al. "Quantitative Gas Chromatographic Analysis of Volatile Fatty Acids in Spent Culture Media and Body Fluids", J Clin. Microbiol., 1986, pp. 523–530.*

(Continued)

*Primary Examiner*—Yelena G. Gakh
(74) *Attorney, Agent, or Firm*—Marger Johnson & McCollom, P.C.

(57) ABSTRACT

A method for determining the presence of an infection in a liquid sample comprising the steps of: lowering the pH of the liquid sample so as to drive short-chain fatty acids present in the liquid sample, acetic acid in particular, to the gaseous phase; detecting short-chain fatty acids, ammonia and, optionally amine species present as gases in a headspace associated with the liquid sample using a detector which is sensitive to the presence of short-chain fatty acids, ammonia and, optionally, amine species, particularly conductive and semi-conductive polymer sensors; and correlating the presence of detected short-chain fatty acids, ammonia and, optionally, amine species with the presence of the infection.

23 Claims, 5 Drawing Sheets

OTHER PUBLICATIONS

Molly et al. "Development of a 5-step multi-chamber reactor as a simulation of the human intestinal microbial ecosystem", Appl. Microbiol. Biotechnol., 1993, v. 39, pp. 254-258.*

Chandiok et al. "Screening for Bacterial Vaginosis": a Novel Application of Artificial Nose Technology", J. Clin. Pathol., 1997, v. 50, No. 9pp. 790-795.*

Pavlou et al. "An intelligent rapid odor recognition model in discrimination of Helicobacter pylori and other gastroesophageal isolates in vitro", Biosens. Bioelectron., 2000, v. 15, pp. 333-342.*

Hayward, N.J., et al., "Head-Space/Gas-Liquid Chromatography in Clinical Microbiology with Special Reference to the Laboratory Diagnosis of Urinary Tract Infections," Gas Chromatography 7 Mass Spectrum. Appl. Microbiol, 1984, pp. 237-255, XP000923009, p. 241, line 1-p. 243, paragraph 2.

Pavlou, A.K., et al., "Sniffing Out the Truth: Clinical diagnosis using the electronic nose," Clinical Chemistry and Laboratory Medicine, vol. 38, No. 2, Feb. 2000, pp. 99-112, XP001061838, ISSN: 1434 6621, p. 103, right-hand column, paragraph 2, p. 104, left-hand column, paragraph 2, figure 7.

Aathithan, S., et al., "Diagnosis of bacteriuria by detection of volatile organic compounds in urine using an automated headspace analyzer with multiple conducting polymer sensors," Journal of Clinical Microbiology, vol. 39, No. 7, Jul. 2001, pp. 2590-2593, XP002192447, ISSN: 0095-1137, whole document.

Guernion, Nicolas, et al., "Identifying bacteria in human urine: Current practice and the potential for rapid, near-patient diagnosis by sensing volatile organic compounds," Clinical Chemistry and Laboratory Medicine, vol. 39, No. 10, Oct. 2001, pp. 893-906, XP 001061839, ISSN: 1434-6621, p. 898, right-hand column, paragraph 2—p. 899, right-hand column, paragraph 3; table 4.

Coloe, P.J., "Ethanol Formed from Arabinose: A Rapid Method for Detecting Escherichia Coli," Journal of Clinical Pathology, London, GB, vol. 31, 1978, pp. 361-364, XP000922894, ISSN: 0021-9746, abstract.

Haywood, N.J., et a l., "Assessment of Technique for Rapid Detection of Escherichia Coli And Proteus Species in Urine by Head-Space Gas-Liquid Chromatography," Journal of Clinical Microbiology, Washington, D.C. vol. 6, No. 3, Sep. 1977, pp. 202-208, XP000922891, ISSN: 0095-1137 abstract.

Davies, T. J. and Hayward, N.J., "Volatile Products from Acetylcholine as Markers in the Rapid Urine Test Using Head-Space Gas-Liquid Chromatography," Journal of Chromatography, vol. 307, 1984, pp. 11-21.

* cited by examiner

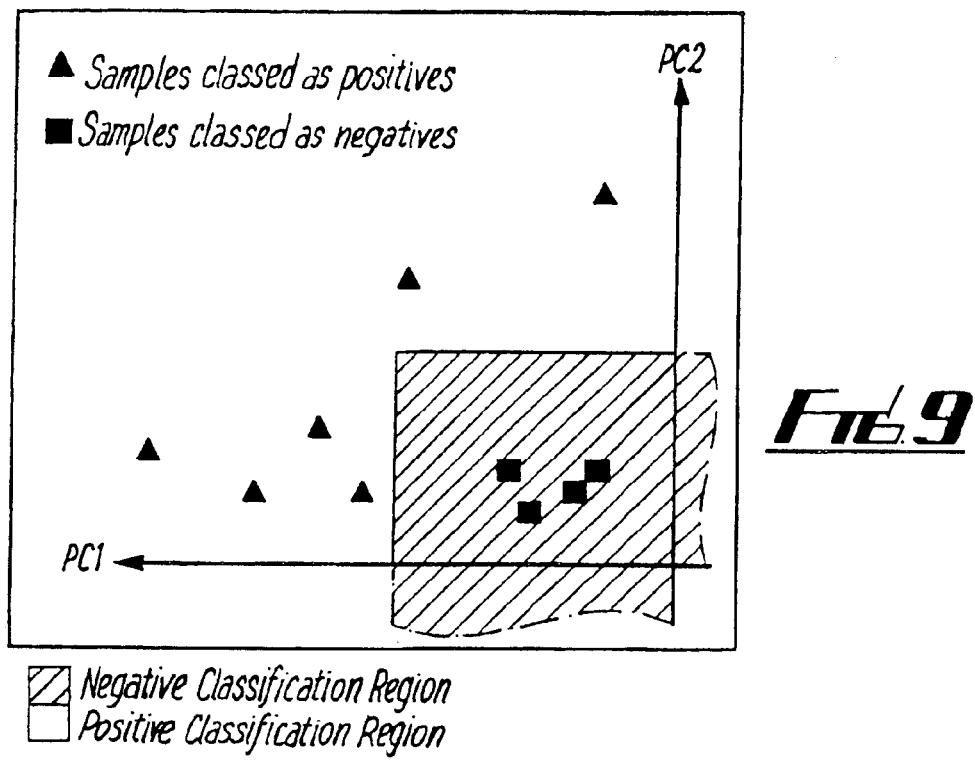
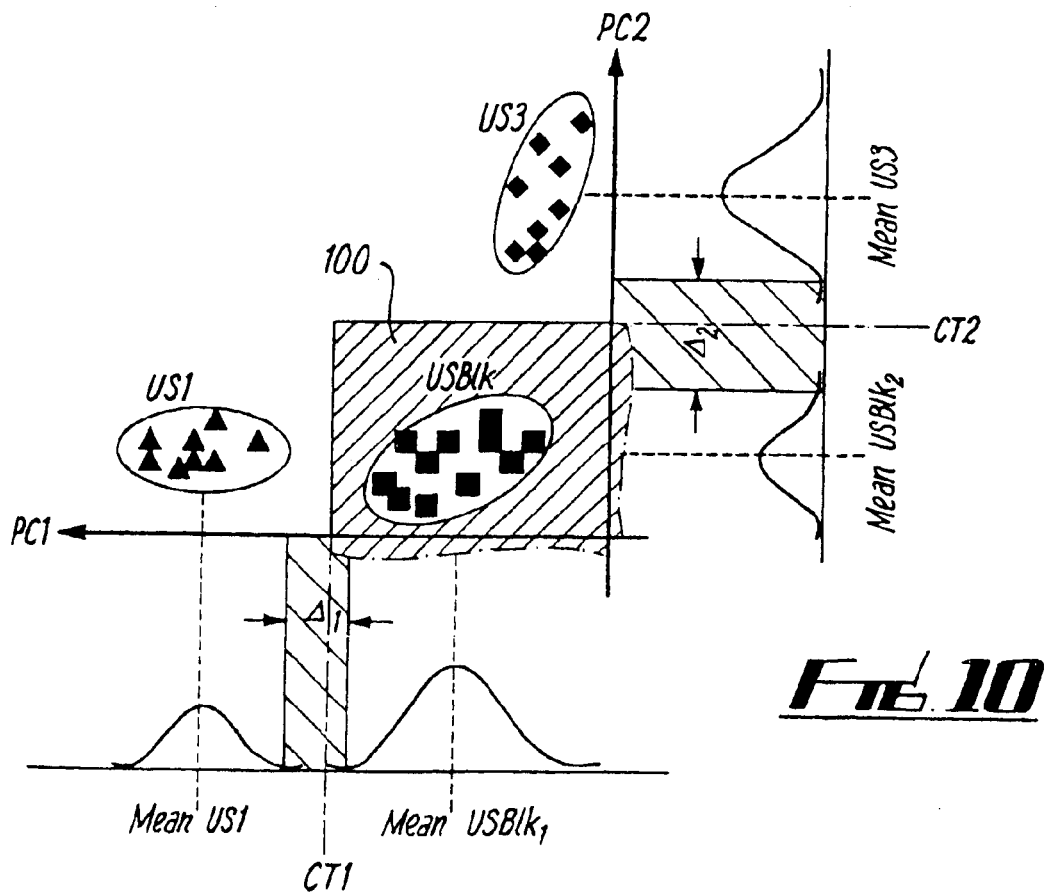

DETERMINING INFECTIONS IN LIQUID SAMPLES BY DETECTING SHORT-CHAIN FATTY ACIDS AND AMMONIA IN THE HEADSPACE ASSOCIATED WITH THE LIQUID SAMPLE USING POLYMER SENSORS

This invention relates to the detection of the presence of an infection in a liquid sample using a gas detector, with particular, but by no means exclusive, reference to the detection of urinary tract infection.

It is known from the applicant's International Application No. WO 95/33848 that microorganisms can be detected using arrays of gas sensors to detect characteristic gases or vapours produced by the microorganisms. An example of such an array is an array of semiconducting organic polymer gas sensors. The applicant's International Applications Nos. WO 98/29563 and WO 98/39470 describe further aspects and refinements to the technique, and related developments. In general, the approach with arrays of gas sensors is to utilise a large number (twenty, thirty or more) of different gas sensors which possesses different but overlapping sensitivities towards different gaseous species (so-called "electronic noses"). Gases are recognised from the characteristic "fingerprint" or pattern of response across the array. However, detection can be difficult in a complex system having mixed populations of microflora and microfaunae and/or systems in which many volatile species are present.

There are more than two hundred different volatile organic compounds present in human uninfected urine. Although it is known to be a possibility that urine from patients with urinary tract infections may have a characteristic profile of volatile organic compounds due to the presence of distinctive bacterial metabolites, previous work in this area has not lead to a practical application of this method.

Manja and Rao (J. Clin. Microbiol. 17 (1983) 264) performed conventional gas-liquid chromatography (GLC) on urine samples incubated with appropriate supplements and showed that the *E. coli* could be identified by the production of ethanol from lactose, and *Klebsiella* species by the production of ethanol from adonitol. Hayward and colleagues (J. Clin. Microbiol., 6 (1977) 195; J. Clin. Microbiol., 6 (1977) 202; J. Chromatogr., 274 (1983) 27; J. Chromatogr., 307 (1984)11) utilised head space gas-liquid chromatography (HS-GLC) to identify volatile bacterial metabolites in artificial cultures and urine. *Proteus* species characteristically produced dimethyl disulfide and methyl mercaptan from L-methionine, and trimethylamine from acetylcholine; *E. coli* and other coliforms produced ethanol from lactose or arabinose. This system was moderately successful in distinguishing infected and uninfected urine by direct analysis, but better results were obtained after incubating with arabinose and acetylcholine. Barrett et al (J. Clin. Pathol. 31(9) (1978) 859) used gas liquid chromatography to analyse clinically infected urines. Acetic acid was the only compound found consistently and it enabled $10^6$ microorganisms per ml to be detected. However, urinary tract infection is diagnosed by the presence of $10^5$ organisms per ml or more, and thus the authors concluded that their method was insufficiently sensitive for the detection of bacteriurea. Furthermore, *Pseudomonas aeruginosa* and *Candida albicans* were not detectable at all.

None of the work described above in the area of urinary tract infection has led to a practical detection method. It is possible that this failure is due to one or more of the following reasons: a lack of instrument sensitivity; failure to discriminate complex volatile mixtures; and failure to identify suitable "marker" volatiles, which are reliably indicative of infection.

The present invention overcomes the above-mentioned problems and difficulties, and provides a quick, reliable and practical screening technique for the detection of urinary tract infection (UTI). The technique is easily automated and may be performed by unskilled operatives with a minimum of technical back-up. It will become apparent that the technique may be applicable to the detection of other infections as well.

For the avoidance of doubt, the terms "gas" and "gases" are understood to embrace all species present in the gas phase, including volatile species emanating from liquids and sublimed species emanating from solids.

According to the invention there is provided a method for detecting the presence of an infection in a liquid sample comprising the steps of:

lowering the pH of the liquid sample so as to drive fatty acids present in the liquid sample into the gaseous phase;

detecting fatty acids, ammonia and, optionally, amine species present as gases in a headspace associated with the liquid sample using a detector which is sensitive to the present of fatty acids, ammonia and, optionally, amine species; and correlating the presence of the detected fatty acids, ammonia and, optionally, amine species with the presence of the infection.

Surprisingly, this relatively small set of "marker" species has been found to be indicative of a range of infections, and has enabled the provision of a detection technique having the aforesaid advantages. Furthermore, it is surprising that ammonia (and/or amine marker species) can be detected with sufficient sensitivity despite the acidification of the source.

The liquid sample may be, or may be derived from, a body fluid. The infection may be a urinary tract infection and the liquid sample may be, or may be derived from, a urine sample. However, it is possible that other infections may be detected using the "markers" disclosed above.

Infection by any of the microorganisms *Proteus mirabilis, Staphylococcus aureus, Staphylococcus saprophyticus, Eschericia coli, Klebsiella pneumoniae* and *Enterococcus faecalis* may be detectable.

The detector may be sensitive to gaseous acetic acid, and the presence of acetic acid, ammonia and, optionally, amine species may be correlated with the presence of the infection. Acetic acid has been found to be the most important fatty acid marker (ammonia being a more most important marker than amine species). The detector may comprise semiconducting organic polymer.

The detector may comprise an array of gas sensors. An array, in the context of the present invention, is two or more gas sensors. In contrast to conventional electronic noses, it has been found that arrays having only a small number of physically different gas sensors can be used advantageously. For example, an array may comprise five or fewer sensor types which are sensitive to fatty acids, and five or fewer sensor types which are sensitive to ammonia (and/or amines). As few as four different sensor types have been found to be sufficient.

The array may comprise gas sensors having semiconducting organic polymer as a gas sensitive layer.

The detector may comprise at least one conductimetric gas sensor having a gas sensitive layer onto which gases absorb and desorp, and in which analytes are detected by:

exposing the gas sensor to the headspace, thereby allowing the adsorption of analytes present in the headspace onto the gas sensitive layer; and making conductimetric measurements of the sensor during a desorption phase in which there is net desorption of analyte from the gas sensitive layer. This approach has been found to be extremely advantageous in terms of improving sensitivity and reproducibility. The principal reason for this is that the effect of water vapour appears to be substantially eliminated in the desorption phase. This is a considerable advantage, and significantly enhances the detection of fatty acids, ammonia and amines. However, it will be appreciated that this approach is not limited to the detection of these species, and nor is it limited to the method of the present invention. Rather, the approach of making conductimetric measurements in the desorption phase can be employed as a general technique for detecting analytes using conductimetric gas sensors which have a gas sensitive layer. Typically, a pulse of gas from the headspace is flowed over the sensor, and the desorption phase commences once this pulse of gas has finished flowing over the sensor.

The conductimetric gas sensor or sensors may comprise semiconducting organic polymer.

This method may further comprise the steps of:

projecting the output of the detector onto the reference PCA map using the reference loadings.

This approach permits very convenient and quick assessment of whether a sample is infected on the basis of simple assessment criteria. Furthermore, it is possible to calibrate the system and to perform self-test protocols using this approach.

The reference PCA map may comprise a two dimensional map in which one PCA axis is correlated to the presence of fatty acids and the other PCA axis is correlated to the presence of ammonia and, optionally, amine species. Intensity data from the detector may be projected onto the reference PCA map so that position along the PCA axis is related to the concentration in the headspace of the species which is correlated to that PCA axis. In this way the intensity data can be related to the concentration of marker species which in turn can be related to the number of infecting organisms. In particular, it is possible to observe if a threshold concentration has been crossed, allowing the correlation of detector output with the presence of infection to be made. It should be noted that in the prior art, intensity data from electronic noses comprising arrays of gas sensors are usually removed by normalisation before analysis such as PCA, so that concentration independent "fingerprints" can be obtained.

Methods in accordance with the invention will now be described with reference to the accompanying drawings, in which:

FIG. 9 shows the classification of liquid samples, from data projected onto a classification map; and FIG. 10 shows sample classification using PCA mapping.

Figure 1:
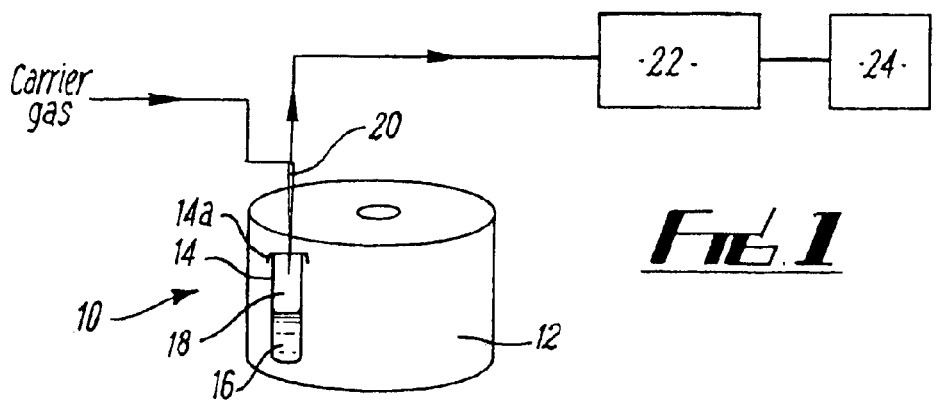
FIG. 1 is a schematic diagram of apparatus suitable for identifying the presence of an infection in a liquid sample.

FIG. 1 schematically depicts apparatus shown generally at 10, for use with the method of the present invention. The apparatus comprises a sample carousel 12 in which a number of sample vials can be mounted and maintained at a constant temperature, for example 30° C. For simplicity, a single sample vial 14 is shown in FIG. 1. The vial 14 contains a liquid sample 16. Above the liquid sample 14 is a gaseous headpsace 18 which contains inter alia volatile species emanating from the liquid sample 16. For reasons which are explained in more detail below, the liquid sample 16 is acidified before being introduced into the carousel 12 so as to drive fatty acids present in the liquid sample into the gaseous phase and thus into the headspace 18.

The vial 14 has a septum 14a thereon which is pierced by a needle 20, the insertion of needle 20 into the vial 14 being performed automatically by the apparatus 10. The needle 20 is of co-axial design, which permits a carrier gas (such as air, nitrogen or a noble gas) to be introduced to vial 14 via one of the lumen of the needle 20. Gases in the headspace 18 are entrained in the flow of carrier gas, which exits the vial 14 via the other lumen of the needle 20, and thereafter is flowed across a gas sensor array 22. In this way, the headspace 18 is sampled by a gas detector 22, which in this embodiment is a gas sensor array. It will be appreciated by the skilled reader that there are many other ways in which the headspace might be coupled to a gas detector—for example, carrier gas might be introduced to the vial 14 through a conduit which protrudes into the liquid sample 16, thus "bubbling" the carrier gas through the liquid sample 16, and exit through a separate aperture which is separated from the liquid sample 16. This is a so-called "sparging" technique. Additionally, the use of devices such as filters and preconcentrators is feasible.

The gas sensor array 22 is selected so that it can detect fatty acids, in particular acetic acid, ammonia and, optionally, amine species. These species constitute the "marker" species which, it has been found, can be indicative of infection.

The output of the gas sensor array 22 is monitored and analysed by control means 24 which comprise computer means or other microprocessor-based analysis means. The control means 24 can also control the operation of the carousel 12, the flow of carrier gas, washing and calibration procedures, and the manner in which the gas sensor array 22 is operated or interrogated. However, it is quite possible to transfer data from the control means 24 to, for example, a remote computer for analysis. In any event, some form of analysis means is provided which is adapted to correlate the presence of the detected fatty acids, ammonia and, optionally, amine species with the presence of the infection. In this way, the liquid sample 14 is screened for the infection.

The method of the present invention has been used to screen urine samples for urinary tract infections. Human urine is a highly complex mixture comprising many components and species of microorganisms. Some of the components of urine are volatile, and thus the headspace associated with a sample of urine is itself complex. It is known from WO 95/33848 that microorganisms can produce volatile species which are characteristic of the microorganisms. What is not known from WO 95/33848 is how, with a highly complex headspace associated with any urine sample, one can identify the presence of an infection in the urine sample from gases emanating from the sample.

There are a number of microorganisms implicated in urinary tract infection, such as *Proteus mirabilis, Staphylococcus aureus, Staphylococcus saprophyticus, Eschericia coli, Klebsiella pneumoniae* and *Enterococcus faecalis*. Surprisingly, a quite limited set of gaseous "marker" species have been found to be indicative of the presence of urinary tract infection by these agents. The pH of the liquid sample is lowered, typically to a pH of 2.0 or below, often to a pH of around 1.0, in order release fatty acids into the gaseous phase. Surprisingly, even under acidic conditions, it is still possible for ammonia (and volatile amine species) to be evolved in sufficient quantity to be useful as a "marker" species. In fact, the detection of ammonia (and/or volatile amines) is extremely important because such species are indicative of infection by Proteus mirabilis. It is believed that Proteus sp. remains active despite the acidification, and produces ammonia as a metabolite. The presence of ammonia neutralises to some extent the added acid, and thus the pH of samples producing ammonia is somewhat higher than that of samples which are not infected with Proteus sp. Ammonia is typically observed by the gas detector at a pH of around 4 or greater. It is possible to observe both ammonia and acetic acid signals at such pHs. It should be noted that it may be possible to detect additional marker species in order to provide improved detection or even to aid in the identification of specific species.

Preparation of the liquid sample thus includes the addition of an acid, for example, HCl, in sufficient quantity to lower the pH to the desired value. Optionally, a salt such as $Na_2SO_4$ can be added in order to displace less soluable volatiles, in particular organic species, from solution and into the gaseous phase. Since the liquid samples can be highly acidic, often of a pH ca. 1 and often at a temperature above room temperature, proper selection of materials is very important. Nickel is a suitable metal for use in components such as a sampling needle (conventional metals such as stainless steel being too reactive). PTFE can be used elsewhere. Backwashing between samples is advisable to prevent cross-contamination.

In a preferred embodiment, the gas detector is an array of gas sensors, and in a particularly preferred embodiment the gas sensors comprise semiconducting organic polymer gas sensors. However, in principle, other forms of gas detector might be employed, provided that they are sensitive to the marker species described above. As an indication of the sensitivities required, it is noted that a GC/MS analysis performed by the Applicants of 98 samples of urine of which 50% were confirmed positive for bacteria using traditional culture and colony counting methods, indicated that control samples were on average associated with a concentration of 3 ppm acetic acid, 6 ppm being the threshold for false positives, and that the range of positives was from 6–500 ppm, with an average value being about 100 ppm. Gas detection techniques which are candidates for use in the present invention include gas chromatography, mass spectrometry and spectroscopic techniques such as IR spectroscopy. Other forms of gas sensor array might be contemplated, such as arrays of metal oxide sensors, SAW sensors, quartz resonators, "composite" sensors of the type described generally in U.S. Pat. No. 5,571,401, and arrays comprising mixtures thereof.

Embodiments of a preferred—but non-limiting-kind of gas detector will now be described, namely arrays of semiconducting organic polymer gas sensors. As discussed above, the traditional approach with such arrays is to employ a large number (typically twenty or more) of different sensors having different polymers and/or different dopant counterions, thus producing an array in which the individual gas sensors exhibit broad and overlapping sensitivities towards a range of different gases. The same principle applies to other arrays of gas sensors, such as metal oxide sensors. Devices of this type are commonly referred to as "electronic noses".

In direct contrast, it has been found that screening for infection according to the present invention can be advantageously performed using an array which comprises a limited number of sensor types, ie. sensors with physically different polymer/counterion combinations. In one example, four types of selective conducting polymer sensors have been developed and incorporated into a device. Two of these are acid sensitive, one sensitive to ammonia, and the other sensitive to ammonia and trimethyl amine. These four sensor types are incorporated into a 48 sensor array, comprising 12 sets of replicate sensors. The provision of 12 replicates of each sensor type permits signal averaging over a large number of sensors. Additionally, sets of replicate sensors allows the array to function in the event that one or even more than one sensor in any given replicate set malfunctions.

The changes in resistance of each sensor type in response to a volatile sample are recorded with time, and are averaged for each sensor type over the array. It has been observed that it is possible to eliminate the effect of water vapour on the response of the sensors by choosing a portion of the trace corresponding to the desorption phase of the experiment. With acetic acid as the analyte, it has been observed that there is undershoot in the signal below the previous baseline (see FIG. 2a). This effect is reproducible, is a function of concentration of acetic acid, and is a parameter due to the type of materials incorporated into the sensor. The time course is primarily dependent on the sensor kinetics, but carrier flow and header geometry will also have an effect.

Figure 2A:
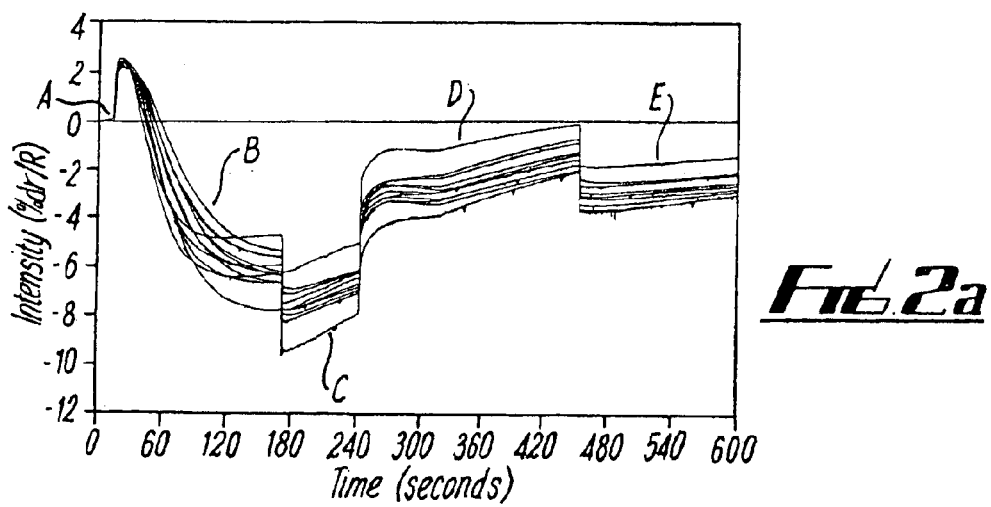
FIG. 2 shows sensor responses a) to acetic acid of one polymer type and b) to ammonia of another polymer type as a function of time.

FIG. 2a shows a number of response profiles to acetic acid for a semiconducting organic polymer sensor against time. The baseline response is indicated at "A". During the period of time indicated as "B", the sensors are exposed to a pulse of gas comprising acetic acid entrained in a carrier gas. This can be regarded as an "adsorption phase" during which there is nett adsorption of acetic acid—and water— onto the sensors. After the gas pulse has finished, there is a desorption phase, or recovery phase, which is indicated as "C", during which there is a nett desorption of analyte from the sensors. It can be seen that the response becomes negative with respect to the baseline during the recovery phase. With fatty acid analytes, signal averaged over the period C is a function of the concentration of acid present in the headspace. The responses shown at "D" and "E" relate to (standard) wash and reference cycles, respectively.

Figure 2B:
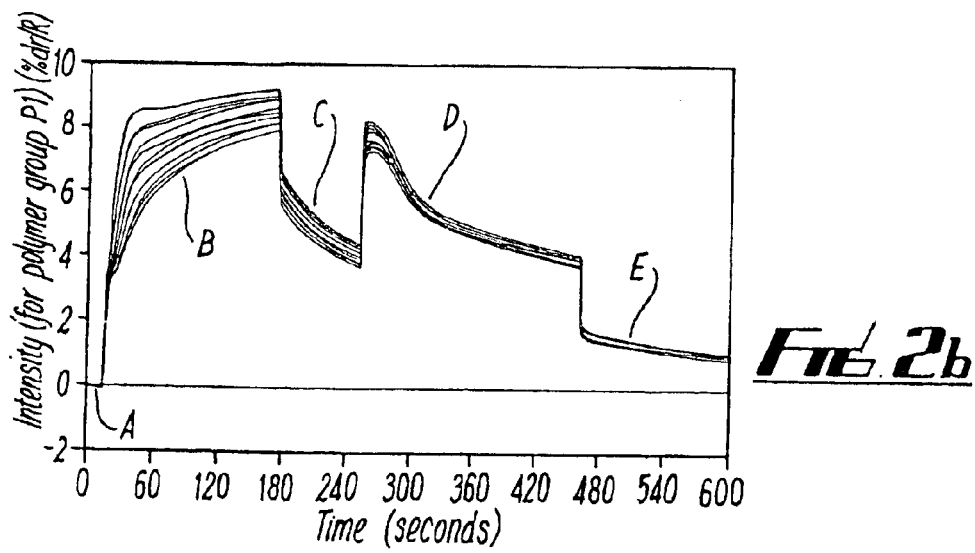

It should be noted that generally similar responses are obtained when the sensors are expected to ammonia (FIG. 2b), ie. there are distinct baseline, adsorption and recovery phases. However, the response in the recovery phase in this instance remains positive with respect to the baseline. Measurements made during the recovery phase are also substantially free from interferences from moisture.

Interference from moisture is a major limitation for a number of gas sensing technologies which interrogate a gas sensitive layer of some kind upon which analytes—and water vapour—can reversibly adsorb. Semiconducting organic polymers are an example of such a gas sensitive layer. The above described technique for rejecting interferring signals due to moisture is of broad significance—not only is the technique applicable in the context of screening for urinary tract infection, it can be utilised more widely in the detection of analytes per se.

It is believed that the displacement of the sensor response from the baseline during the recovery phase is a result of the analyte still being bound at the polymer surface. As a result of interactions between the bound analyte and the electronic structure of the polymer, the polymer can be more doped (producing a negative response) or less doped (producing a positive response) than when the baseline measurements were made. It is believed that water desorbs from the polymer surface very rapidly during the recovery phase, and so most of the recovery phase is substantially moisture free. However, these mechanisms are speculative in nature, and should not be regarded as a limiting one.

It should be noted that, whilst prior art semiconducting organic polymer gas sensors generally show good sensitivity towards ammonia, it has not previously been possible to detect fatty acids such as acetic acid at low concentrations using such gas sensors. The present invention provides new gas sensors which employ new semiconducting organic polymers. With these polymers, high sensitivity towards fatty acids (such as acetic acid) and ammonia can be achieved.

The new materials have a bilayer structure with a baselayer of polypyrrole deposited chemically using ferric chloride as an oxidant. Different sensor types are manufactured by electrochemically depositing different top layer polymers onto this baselayer. The four types of sensors incorporated into the device described above use the following monomer/electrolyte combinations for the electrochemical deposition stage:
 1. 3-Hexanoylpyrrole/tetraethylammonium p-toluenesulponate
 2. 1-Octylpyrrole/tetrabutylammonium triflate
 3. 3-Dodecylpyrrole/Tetraethylammonium tetrafluoroborate
 4. 1-Dodecylpyrrole/Tetraethylammonium tetrafluoroborate The 3-substituted monomers can be synthesised following the method of Ruhe et al (Makromol, Chem., Rapid Commun. 10 (1989) 103). The 1-substituted monomers can be synthesied following the method of Santaniello et al (Synthesis, 1979, 617).

Further details of the polymerisation conditions and of the preparation of polymer bilayers having a baselayer of polypyrrole can be found in the Applicant's earlier International Publication WO 96/00383.

Data Processing

An object of the invention is to produce a rapid screening system for urinary tract infection. The system is capable of making a decision based on the relative intensities of acetic acid and/or ammonia present in the urine headspace. This has been greatly facilitated by a novel data processing technique which is discussed below and which is based on principal components analysis (PCA—see, for example, J E Jackson, J Qual. Tech., 13(1) (1981)). It has been established that if a principal components analysis of the intensity data from the highly orthogonal sensors is carried out, the distribution of points projected on a first principal components axis PCA 1 is correlated to acetic acid, and that the points projected on a second principal components axis PCA 2 are correlated to ammonia. The distribution along either coordinate axis is also a function of the concentration of the analyte in the headspace, and hence of the concentration of marker chemicals produced by the microorganisms present in the sample. This thus gives a simple way of assigning a threshold for deciding whether or not a sample is positive or negative, based on user-defined clinical criteria. For example, $10^5$ cfu's/ml or greater may be taken to constitute an infection (a cfu is a colony forming unit). In broad terms, the data processing comprises using calibration samples to establish a PCA "reference map", and then projecting data obtained from enclosed samples onto this PCA reference map in order to establish if these data are indicative of infection.

Data processing is described in more detail below, with reference to various calibration and measurement process which are performed.

1. Calibration

Calibration is a two-stage process:
 1. Run calibration standards to generate reference map, verify results and store PCA loadings information;
 2. Run calibration standards, project data on to reference map, verify results and calculate the classification thresholds.

In one example the array is calibrated using defined standards consisting of acetic acid (in concentrations of 3, 20 and 100 ppm) in 0.1M HCl/20% $Na_2SO_4$, and ammonium hydroxide (10 ppm) in 0.01M NaOH. 1 ml sample volumes are used as above. Before each main experimental run, subsets of standards are run, each sample cycle lasting 20 minutes.

1.a. Reference Map

Figure 3:
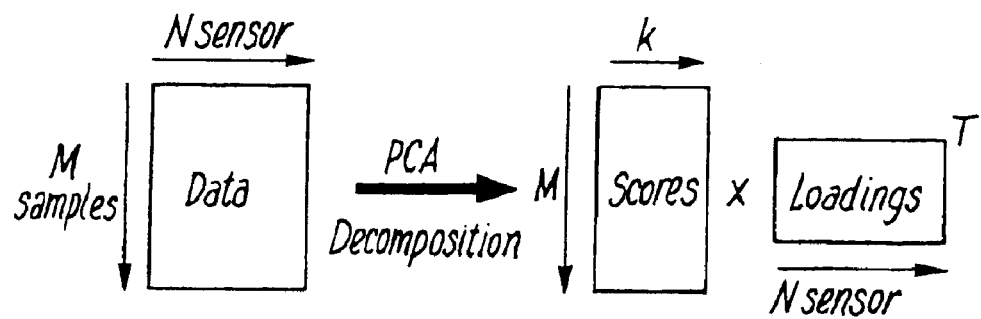
FIG. 3 shows a PCA transformation.
Figure 4:
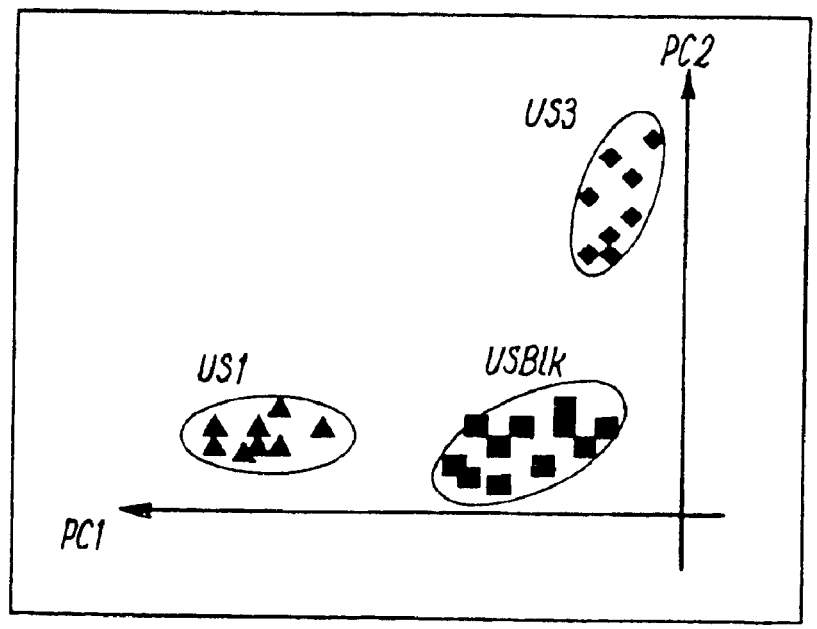
FIG. 4 shows a PCA reference map.

The calibration data is transformed using Principal Component Analysis (PCA) to characterise the instrument sensor responses for the calibrants run, thus defining a two-dimensional mapping space on to which all subsequent samples analysed can be projected. PCA decomposes the original calibrant data matrix into a set of scores and loading vectors, in which scores contain information of how samples relate to one another whilst the loadings show how variables relate to one another. This process is depicted in FIG. 3, and can be written as:

$$X = t \times p^T$$

where t denotes the scores, which are vectors of linear combinations of sensor variables that describe the major trends in the original data matrix X. The loadings, which are represented by p, are a set of orthonormal eigenvectors representing a new set of axes onto which the scores information is projected. In FIG. 3 T denotes the transpose of a matrix. The result is a "reference map" which is shown in FIG. 4.

Figure 5:
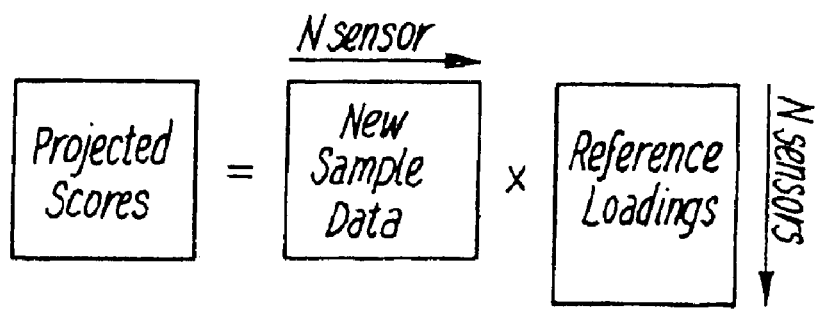
FIG. 5 shows the calculation of projected PCA scores.

Projected scores (PC1 and PC2) can be calculated by multiplying the analysis results with the reference loadings calculated in the calibration step. This process is depicted in FIG. 5.

1.b. Discrimination Check

In the following discussion, USB1k is the 3 ppm acetic acid standard referred to above, US1 is the 20 ppm acetic acid standard referred to above, US2 is the 100 ppm acetic acid standard referred to above, and US3 is the 10 ppm ammonium hydroxide standard referred to above.

Figure 6:
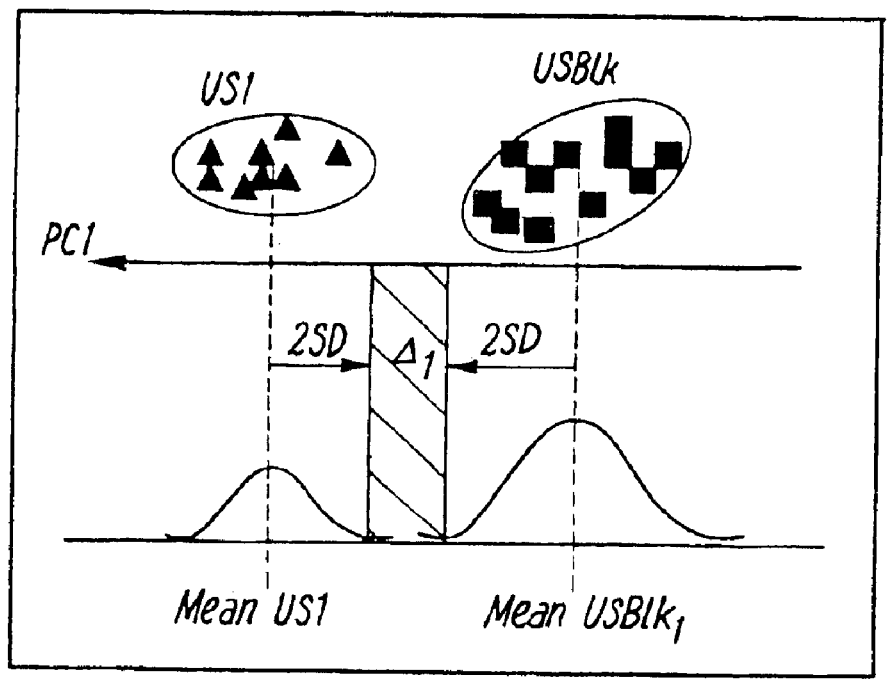
FIG. 6 is a graphical representation of a first discrimination check along the PC1 axis.

Discrimination Check 1: A system check is performed on the calibration data to ensure that there is no overlap between the sample distributions for each of the standards (US1, US3) and the USB1k at the 97.5% confidence interval for the mean of each standard. FIG. 6 depicts such a check for the US1 samples along the PC1 axis.

In FIG. 6, $\Delta_i$ is the degree of separation between the population distribution of US1 and USB1k sample responses along the PC1 axis at the 97.5% confidence level. The following condition must be satisfied to show that the population distribution between the standards are separated:

$$|\text{Mean } US1_{PC1} - \text{Mean } USB1k_{PC1}| > 2 \times (SD\ US1_{PC1} + SD\ USB1k_{PC1})$$
$$|\text{Mean } US3_{PC2} - \text{Mean } USB1k_{PC2}| > 2 \times (SD\ US3_{PC2} + SD\ USB1k_{PC2})$$

This corresponds to $\Delta_i > 0$.

Discrimination Check 2: Once satisfied that there is no overlap between each of the separate clusters, a second check is performed to ensure that the level of discrimination between the standards is above a minimum acceptable discrimination threshold (DT) value, such that:

|Mean $US1_{PC1}$−Mean $USB1k_{PC1}$|>$DT$

|Mean $US3_{PC2}$−Mean $USB1k_{PC2}$|>$DT$

Figure 7:
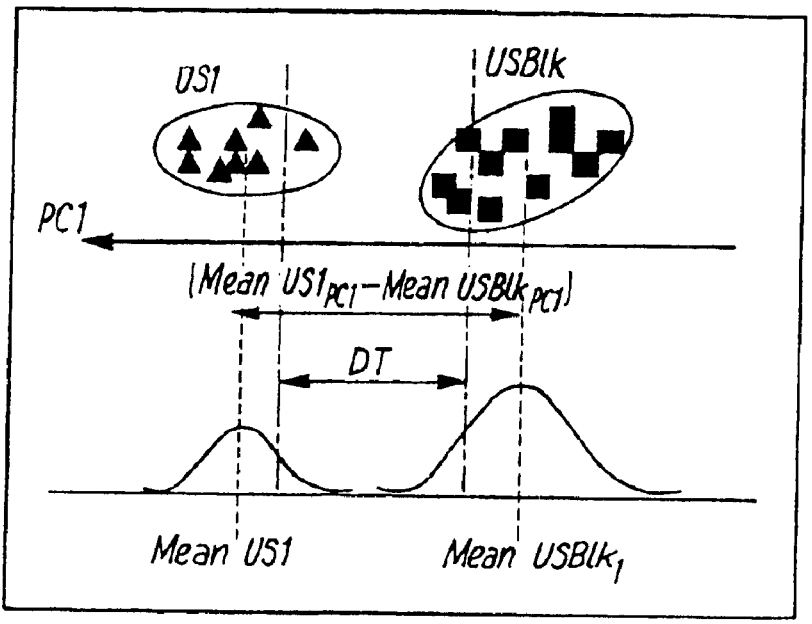
FIG. 7 is a graphical representation of a second discrimination check along the PC1 axis.

This check is depicted in FIG. 7.

1.c. Classification Thesholds

The classification thesholds are defined as:

$CT1$=(Mean $US1_{PC1}$−Mean $USB1k_{PC1}$)/2 (along the PC1 axis)

$CT2$=(Mean $US3_{PC2}$−Mean $USB1k_{PC2}$)/2 (along the PC2 axis)

Figure 8:
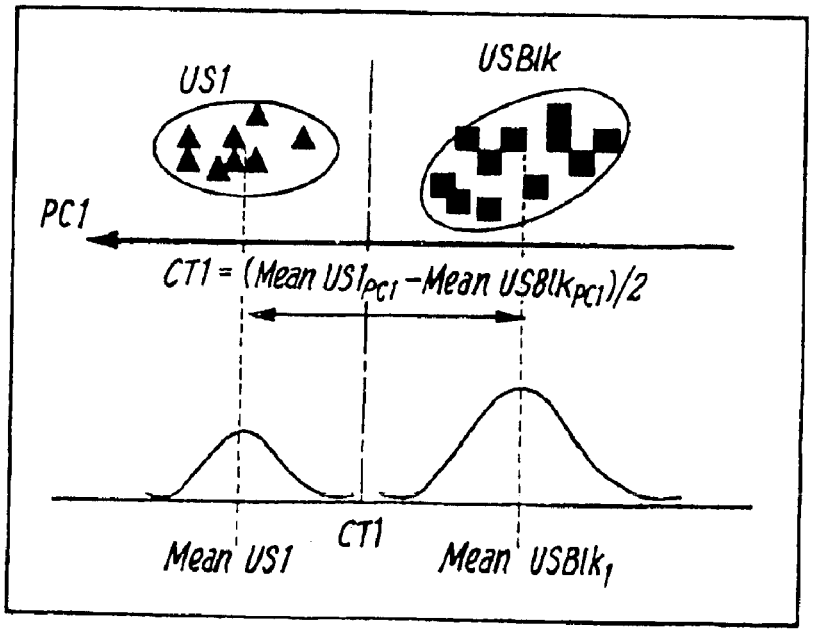
FIG. 8 is a graphical representation of a classification threshold along the PC1 axis.

The classification theshold CT1 (along the PC1 axis) is depicted in FIG. 8.

2. Classification Map

The information provided by the calibration processes is used to construct a "classification map", a representation of which is shown in FIG. 9. The classification map can then be used for sensor check and classifying clinical samples. Samples that lie within the shaded region are then classified as negatives while those that are projected outside the shaded region are classified as positive samples.

A summary of these data processing steps is shown in FIG. 10, in which $\Delta_i$ is the separation between each sample population (i=1,2) and CT is the classification threshold along each principal component axis. The shaded region 100 is the region of the PCA map representating a negative UT1 classification.

Variants to the scheme described above would suggest themselves to the skilled reader. For example, samples may be separated and classified using Mahalanobis distance measure. In principle, more than two principal components might be used to construct the reference map and classification map. Such an approach may not be of great advantage in the context of the technique for detecting urinary tract infection discussed above. However, the data processing principles discussed above may be applicable to the analysis of gas sensors in other application areas and the approach may even be applicable beyond the field of gas sensors, perhaps to the analysis data from combinations of other kinds of sensor, or to multivariate data analysis per se.

EXAMPLE

Sterile pooled human urine (PHU), cultures of common urinary pathogens in PHU and 340 unselected clinical urine specimens (CUS) were analysed using the apparatus described above, and using conventional semi-quantitative plate culture method and the results compared.

Urine samples were analysed in the following way. 1 ml of urine was transferred to a 22 ml vial containing 0.4 ml 1 M HCl and 200 mg of sodium sulphate. The 22 ml sample vial was capped with a PTFE-line silicone septum. The vial was placed in a carousel as shown in FIG. 1 and allowed to equilibrate at 30° C. to allow a consistent generation of sample headspace. The apparatus then automatically inserted a needle through the sample vial septum, in order to analyse the headspace. Nitrogen gas at 50% relative humidity was introduced above the surface of the urine via the inner lumen of the coaxial needle. The sample headspace was sampled through the outer lumen of the needle, and flowed over the sensors at a flow rate of ca. 60 ml min−1. The sensors were allowed to recover before humid nitrogen gas was passed over the sensors for a 4 minute "wash". The resistance of each of the sensors was measured during the recovery period (typically between 220 and 240 seconds after sampling), and the change ($\Delta R$) from the initial resistance (base resistance R), was calculated. The needle was then removed, the carousel moved the next sample into position, and the process was repeated. Each PHU specimen was analysed four times and the results recorded as the mean of the four replicates.

Results PHU containing>$10^5$ cfu/ml of *E. coli, K. pneumoniae, P. mirabilis, S. aureus, S. saprophyticus* or *E. faecalis* were readily distinguished from sterile controls, demonstrating the utility of this method: 76/340 CUS (22%) were positive by conventional culture. 53% of positives contained *E. coli*, 11% *E. faecalis*, 8% *Klebsiella* spp., 5% *Pseudomonas* spp., 3% Group B *Streptococci*, 1% *Proteus* spp., 1% *Candida* spp. and 18% mixed organisms. The sensitivity specificity, NPV and PPV values of the classification were 85.5%, 89.0%, 95.5% and 69.1% respectively. There were 11 false negatives and 29 false positives. The tendency of the system to over report false positives rather than false negatives is desirable in a screening system since all positive specimens are further investigated by conventional methods.

What is claimed is:

1. A method for detecting the presence of an infection in a liquid sample, comprising:

lowering the pH of the liquid sample to drive short-chain fatty acids present in the liquid sample to the gaseous phase;

detecting short-chain fatty acids, ammonia and, optionally amine species present as gases in a headspace associated with the liquid sample using a detector which is sensitive to the presence of atty acids, ammonia and, optionally, amine species in said headspace, said detector comprising an array of gas sensors including at least one sensor from the group consisting of conductive polymer sensors and semiconductive polymer sensors; and correlating the presence of detected short-chain fatty acids, ammonia and, optionally, amine species with the presence of the infection.

2. The method of claim 1 wherein the liquid sample is, or is derived from, a body fluid.

3. The method of claim 2 wherein the infection is a urinary tract infection and the liquid sample is, or is derived from, a urine sample.

4. The method of claim 3 wherein infection by any of the microorganisms *Proteus mirabilis, Staphylococcus aureus, Staphylococcus saprophyticus, Eschericia coli* and *Klebsiella pneumoniae* is detectable.

5. The method of claim 1 wherein the array of gas sensors comprises gas sensors having semiconducting organic polymer as a gas sensitive layer.

6. The method of claim 1 wherein the detector is sensitive to gaseous acetic acid, and in which the presence of acetic acid, ammonia and, optionally amine species is correlated with the presence of the infection.

7. The method of claim 1 wherein the detector comprises semiconducting organic polymer.

8. The method of claim 1 wherein the detector comprises at least one conductimetric gas sensor having a gas sensitive layer onto which gases adsorb and desorp, and in which analytes are detected by:

exposing the gas sensor to the headspace, thereby allowing the adsorption of analytes present in the headspace onto the gas sensitive layer; and making conductimetric measurements of the sensor during a desorption phase in which there is nett desorption of analyte from the gas sensitive layer.

9. The method of claim 8 wherein the conductimetric gas sensor or sensors comprise semiconducting organic polymer.

10. The method of claim 1 wherein:
   a principal component analysis (PCA) of calibration samples is performed to provide reference scores and reference loadings which are used to construct a reference PCA map; and
   the output of the detector is projected onto the reference PCA map using the reference loadings.

11. The method of claim 10 wherein the reference PCA map comprises a two dimensional map in which one PCA axis is correlated to the presence of short-chain fatty acids and the other PCA axis is correlated to the presence of ammonia and, optionally, amine species.

12. The method of claim 11 wherein intensity data from the detector are projected onto the reference PCA map to that position along a PCA axis is related to the concentration in the headspace of the species which is correlated to that PCA axis.

13. A method for determining an infection in a liquid sample, comprising:
   lowering the pH of the liquid sample sufficiently to drive short-chain fatty acids present in the liquid sample to gaseous phase in a headspace above the liquid sample;
   exposing the headspace above the liquid sample to a gas sensor array structured to detect gaseous short-chain fatty acid and gaseous ammonia present in the headspace above the liquid sample;
   detecting a gaseous short-chain fatty acid and gaseous ammonia in the headspace; and
   correlating the presence of the detected gaseous short-chain fatty acid and the detected gaseous ammonia with the presence of the infection.

14. A method according to claim 13 in which the liquid sample is a body fluid or a liquid sample derived from a bodily fluid.

15. The method of claim 13 in which the infection is a urinary tract infection and the liquid sample is a urine sample or a liquid sample derived from a urine sample.

16. The method of claim 15 in which the infection is caused by one or more of the microorganisms consisting of *Proteus mirabilis, Staphylococcus saprophyticus, Eschericia coli* and *Klebsiella pneumoniae*.

17. The method of claim 13 in which the gas sensor array comprises a plurality of gas sensors having semiconducting organic polymer as a gas sensitive layer.

18. The method of claim 13 in which the gas sensor array comprises a semiconducting organic polymer.

19. The method of claim 13 in which detecting a gaseous short-chain fatty acid and gaseous ammonia in the headspace comprises:
   exposing the headspace above the liquid sample to a gas sensor array including at least one conductimetric gas sensor having a gas sensitive layer onto which gases adsorb and desorp;
   allowing the adsorption of gaseous analytes present in the headspace onto the gas sensitive layer; and
   making conductimetric measurements of the sensor during a desorption phase in which there is net desorption of analyte from the gas sensitive layer.

20. The method of claim 19 in which the conductimetric gas sensor comprises a semiconducting organic polymer.

21. The method of claim 13 in which:
   a principal component analysis (PCA) of calibration samples is performed to provide reference scores and reference loadings are used to construct a reference PCA map; and
   the output of the detector is projected onto the reference PCA map using the reference loadings.

22. The method of claim 21 in which the reference PCA map includes a two-dimensional map in which a first PCA axis is correlated to the presence of fatty acids and a second PCA axis is correlated to the presence of ammonia.

23. The method of claim 22 in which intensity data from the detector are projected onto the reference PCA map so that a position along a PCA axis is related to a concentration in the headspace of the detected species which is correlated to that PCA axis.

* * * * *

UNITED STATES PATENT AND TRADEMARK OFFICE
CERTIFICATE OF CORRECTION

PATENT NO.       : 6,921,668 B2                                         Page 1 of 1
APPLICATION NO.  : 10/221920
DATED            : July 26, 2005
INVENTOR(S)      : Paul James Travers et al.

It is certified that error appears in the above-identified patent and that said Letters Patent is hereby corrected as shown below:

Page 2, Item [63] Other Publications:
insert: -- Barrett, E., et al., "Gas liquid chromatography for detection of bacteriuria: examination for volatile acidic and neutral compounds," Journal of Clinical Pathology, Vol. 31, No. 9, 1978, pages 859-865--

Column 10, line 19, claim 1, "detecting" should be --determining--;
Column 10, line 27, claim 1, "atty" should be --short-chain fatty--.
Column 11, line 14, claim 12, "to" should be --so--.
Column 12, line 1, claim 16 "*Staphylococcus saprophyticus*," should be
--*Staphylococcus aureus, Staphylococcus saprophyticus,*--.
Column 12, line 32, claim 22, "fatty" should be --short-chain fatty--.

Signed and Sealed this

Seventeenth Day of April, 2007

JON W. DUDAS
*Director of the United States Patent and Trademark Office*